United States Patent [19]
Ciliberto et al.

[11] Patent Number: 5,849,283
[45] Date of Patent: *Dec. 15, 1998

[54] HUMAN INTERLEUKIN-6 RECEPTOR ANTAGONISTS

[75] Inventors: Gennaro Ciliberto; Rocco Savino; Armin Lahm; Carlo Toniatti, all of Rome, Italy

[73] Assignee: Istituto di Ricerche di Biologia Molecolare P. Angeletti S.p.A., Rome, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 693,182
[22] PCT Filed: Dec. 13, 1995
[86] PCT No.: PCT/IT95/00216
  § 371 Date: Aug. 14, 1996
  § 102(e) Date: Aug. 14, 1996
[87] PCT Pub. No.: WO96/18648
  PCT Pub. Date: Jun. 20, 1996

[30] Foreign Application Priority Data

Dec. 14, 1994 [IT] Italy .................................. M94A00805

[51] Int. Cl.$^6$ ........................... C07K 14/54; A61K 38/19
[52] U.S. Cl. ............................. 424/85.2; 530/351; 514/2; 514/8; 514/12; 930/141; 435/252.3; 435/252.33; 435/320.1; 435/69.52; 435/71.1; 435/71.2; 435/172.1; 435/172.3
[58] Field of Search ................. 435/69.52, 71.1, 435/71.2, 172.1, 172.3, 252.3, 252.33, 320.1; 530/351; 424/85.2; 514/2, 8, 12; 930/141

[56] References Cited

FOREIGN PATENT DOCUMENTS

94/09138 4/1994 WIPO .
94/11402 5/1994 WIPO .

OTHER PUBLICATIONS

Savino, Rocco et al. "Generation of interleukin 6 receptor antagonists by molecular–modeling guided mutagenesis of residues important for gp130 activation." The Embo Journal, vol. 13, No. 6, pp. 1357–1367 (1994).

Savino, Racino et al., "Saturation mutagenesis of the human interleukin 6 receptor binding site: implications for its three–dimensional structure." Proc. Natl. Acad. Sci., vol. 90, pp. 4067–4071, (May 1993).

Ehlers, Marc et al., "Identification of two novel regions of human IL–6 responsible for receptor binding and signal transduction." Journal of Immunology, vol. 153, No. 4, (Aug. 1994).

Cunningham et al. (1989) Science vol. 244, pp. 1081–1084.

Cwirla et al. (1990) PNAS, vol. 87, pp. 6378–6382.

Primary Examiner—John Ulm
Assistant Examiner—Prema Mertz
Attorney, Agent, or Firm—Browdy and Neimark

[57] ABSTRACT

It is known that the ligands of the group of cytokines similar to Interleukin 6 (IL-6), that is Oncostatin M (OSM), Leukemia Inhibitory Factor (LIF), Ciliary Neurotrophic Factor (CNTF) and Interleukin 11 (IL-11), induce the formation of a receptor complex of which the membrane molecule gp 130 is a part. The present invention refers to a methodology for selecting superagonists, antagonists and superantagonists of human interleukin-6 comprising the following operations: comparing the amino acid sequence of bovine granulocyte colony stimulating factor (bG-CSF) with the sequence of said hormone; and on the basis of the above comparison, formulating a three dimensional model of said hormone, which allows the identification of residues that form the site of interaction with the specific receptor (Site 1) and those that constitute the site of interaction with gp 130 (Site 2) respectively. The invention allows the identification of these sites in human interleukin-6 and the isolation of variants having, with respect to the wild type hormone, a greater affinity for the specific receptor (superagonists and superantagonists) or affinity for gp 130 reduced or abolished (antagonists and superantagonists). The figure shows a scheme illustrating the methodology applied to identify site 1 and site 2 in the case of human interleukin-6. The invention also describes the obtaining of specific superagonists and superantagonists of interleukin-6 and the use of superantagonists as low dose inhibitors of the growth of human myeloma cells dependent on wild type interleukin-6. (FIG. 1)

7 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 555 base pairs
      ( B ) TYPE: nucleic acid
      ( C ) STRANDEDNESS: single
      ( D ) TOPOLOGY: linear ( i i ) MOLECULE TYPE: cDNA (ix) FEATURE:
    (A) NAME/KEY: CDS
    (B) LOCATION: 1..552

(xi) SEQUENCE DESCRIPTION: SEQ ID NO:1:

```
CCA  GTA  CCC  CCA  GGA  GAA  GAT  TCC  AAA  GAT  GTA  GCC  GCC  CCA  CAC  AGA    48
Pro  Val  Pro  Pro  Gly  Glu  Asp  Ser  Lys  Asp  Val  Ala  Ala  Pro  His  Arg
 1              5                        10                       15

CAG  CCC  CTC  ACG  AGC  TCA  GAA  CGA  ATT  GAC  AAA  CAA  ATT  CGG  TAC  ATC    96
Gln  Pro  Leu  Thr  Ser  Ser  Glu  Arg  Ile  Asp  Lys  Gln  Ile  Arg  Tyr  Ile
               20                        25                       30

CTC  GAC  GGC  ATC  TCA  GCC  TTA  AGA  AAG  GAG  ACA  TGT  AAC  AAG  AGT  AAC   144
Leu  Asp  Gly  Ile  Ser  Ala  Leu  Arg  Lys  Glu  Thr  Cys  Asn  Lys  Ser  Asn
               35                        40                       45

ATG  TGT  GAA  AGC  AGC  AAA  GAG  GCA  CTG  GCA  GAA  AAC  AAC  CTG  AAC  CTT   192
Met  Cys  Glu  Ser  Ser  Lys  Glu  Ala  Leu  Ala  Glu  Asn  Asn  Leu  Asn  Leu
     50                        55                        60

CCA  AAG  ATG  GCT  GAA  AAA  GAT  GGA  TGC  TTC  CAA  TCT  GGA  TTC  AAT  GAG   240
Pro  Lys  Met  Ala  Glu  Lys  Asp  Gly  Cys  Phe  Gln  Ser  Gly  Phe  Asn  Glu
 65                       70                        75                       80

GAG  ACT  TGC  CTG  GTG  AAA  ATC  ATC  ACT  GGT  CTT  TTG  GAG  TTT  GAG  GTA   288
Glu  Thr  Cys  Leu  Val  Lys  Ile  Ile  Thr  Gly  Leu  Leu  Glu  Phe  Glu  Val
                    85                        90                       95

TAC  CTA  GAG  TAC  CTC  CAG  AAC  AGA  TTT  GAG  AGT  AGT  GAG  AGT  CAA  GCC   336
Tyr  Leu  Glu  Tyr  Leu  Gln  Asn  Arg  Phe  Glu  Ser  Ser  Glu  Ser  Gln  Ala
               100                       105                      110

AGA  GCT  GTC  CAG  ATG  AGT  ACA  AAA  GTC  CTG  ATC  CAG  TTC  CTG  CAG  AAA   384
Arg  Ala  Val  Gln  Met  Ser  Thr  Lys  Val  Leu  Ile  Gln  Phe  Leu  Gln  Lys
               115                       120                      125

AAG  GCA  AAG  AAT  CTA  GAT  GCA  ATA  ACC  ACC  CCT  GAC  CCA  ACC  ACA  AAT   432
Lys  Ala  Lys  Asn  Leu  Asp  Ala  Ile  Thr  Thr  Pro  Asp  Pro  Thr  Thr  Asn
     130                       135                       140

GCC  AGC  CTG  CTG  ACG  AAG  CTG  CAG  GCA  CAG  AAC  CAG  TGG  CTG  CAG  GAC   480
Ala  Ser  Leu  Leu  Thr  Lys  Leu  Gln  Ala  Gln  Asn  Gln  Trp  Leu  Gln  Asp
145                       150                       155                      160

ATG  ACA  ACT  CAT  CTC  ATT  CTG  AGA  TCT  TTT  AAG  GAG  TTC  CTG  CAG  TCC   528
Met  Thr  Thr  His  Leu  Ile  Leu  Arg  Ser  Phe  Lys  Glu  Phe  Leu  Gln  Ser
                    165                       170                      175

AGC  CTG  AGG  GCT  CTT  CGG  CAA  ATG  TAG                                       555
Ser  Leu  Arg  Ala  Leu  Arg  Gln  Met
               180
```

(2) INFORMATION FOR SEQ ID NO:2:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO:2:

```
Pro  Val  Pro  Pro  Gly  Glu  Asp  Ser  Lys  Asp  Val  Ala  Ala  Pro  His  Arg
 1              5                        10                       15

Gln  Pro  Leu  Thr  Ser  Ser  Glu  Arg  Ile  Asp  Lys  Gln  Ile  Arg  Tyr  Ile
               20                        25                       30

Leu  Asp  Gly  Ile  Ser  Ala  Leu  Arg  Lys  Glu  Thr  Cys  Asn  Lys  Ser  Asn
               35                        40                       45

Met  Cys  Glu  Ser  Ser  Lys  Glu  Ala  Leu  Ala  Glu  Asn  Asn  Leu  Asn  Leu
     50                        55                        60

Pro  Lys  Met  Ala  Glu  Lys  Asp  Gly  Cys  Phe  Gln  Ser  Gly  Phe  Asn  Glu
```

-continued

```
              65                            70                            75                            80
Glu  Thr  Cys  Leu  Val  Lys  Ile  Ile  Thr  Gly  Leu  Leu  Glu  Phe  Glu  Val
                    85                            90                            95

Tyr  Leu  Glu  Tyr  Leu  Gln  Asn  Arg  Phe  Glu  Ser  Ser  Glu  Ser  Gln  Ala
                    100                           105                           110

Arg  Ala  Val  Gln  Met  Ser  Thr  Lys  Val  Leu  Ile  Gln  Phe  Leu  Gln  Lys
                    115                           120                           125

Lys  Ala  Lys  Asn  Leu  Asp  Ala  Ile  Thr  Thr  Pro  Asp  Pro  Thr  Thr  Asn
          130                      135                      140

Ala  Ser  Leu  Leu  Thr  Lys  Leu  Gln  Ala  Gln  Asn  Gln  Trp  Leu  Gln  Asp
145                           150                           155                           160

Met  Thr  Thr  His  Leu  Ile  Leu  Arg  Ser  Phe  Lys  Glu  Phe  Leu  Gln  Ser
                    165                           170                           175

Ser  Leu  Arg  Ala  Leu  Arg  Gln  Met
                    180
```

(2) INFORMATION FOR SEQ ID NO:3:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GTGAGAGCTC  CAAAGAGGCA  CTGGCAGAAA  ACAACCTGAA  CCTTCCAAAG  ATGGCTGAAA        60

AANNSGGATG  CNNSNNSNNS  GGATTCAATG  AGGAG                                     95
```

(2) INFORMATION FOR SEQ ID NO:4:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GGCCTCTAGA  TATACCTCAA  ACTCCAAAAG  ACCAGTGATG  ATTTTCACCA  GGCAAGTCTC        60

CTCATTGAAT  CC                                                                72
```

HUMAN INTERLEUKIN-6 RECEPTOR ANTAGONISTS

DESCRIPTION

The present invention relates to a methodology for selecting superagonists, antagonists and superantagonists of human interleukin-6 (hereinafter referred to also as h IL-6 or IL-6) based on three-dimensional modelling.

As is known, WO 92/21029 to Genentech Inc. teaches a method for determination of agonists or antagonists of growth hormones and ligands with a similar structural conformation. The potential agonists and antagonists are put into contact with a receptor for the hormone and this causes formation of a ternary complex consisting of a molecule of the potential agonist or antagonist and two molecules of such receptor for the hormone to be agonized or antagonized. Dimerization of receptors induced by a ligand molecule allows to conclude that the ligand has two different interaction sites (site 1 and site 2), on which it is possible to operate using mutagenesis to generate agonists or antagonists.

It is known that the ligands in the group of cytokines similar to Interleukin 6 (IL-6), that is Oncostatin M (OSM), Leukemia Inhibitory Factor (LIF), Ciliary Neurotrophic Factor (CNTF), and Interleukin 11 (IL-11), induce the formation of a receptor complex of which the membrane molecule gp 130 is a part. In this receptor complex the specific receptor for each of these cytokines and the membrane molecule gp 130 are always present as common elements. It is thus possible to formulate the hypothesis that site 1 and site 2 bind to two different molecules in this class of hormones: site 1 to the specific receptor and site 2 to gp 130. Identification of the two sites is made possible, as will be seen more clearly from the following, by construction of a three-dimensional model of the receptor complex based on the functional similarity between sequences of the human growth hormone (hGH) receptor and sequences of the receptors for the hormones in question. Isolation of variants that, with respect to the wild type hormone, have a greater affinity for the specific receptor (superagonists or superantagonists) is obtained by construction of filamentous phage libraries, for example M13, carrying the hormone, both in the wild type and mutant version.

According to the invention, the difference between the three-dimensional model, for example of IL-6, adopted here and the one adopted in WO92/21029 leads to identify different residues in helix A and C as constituents of site 2. In fact, for the construction of the IL-6 model according to present invention the structure of a different cytokine instead of growth hormone, was used as template.

Modelling of the human interleukin 6 molecule is performed as follows. It is known, from data available in scientific literature, that the amino acid sequence of human interleukin 6 shows similarities with that of the granulocyte colony stimulating factor (G-CSF). The three-dimensional structure of bovine granulocyte colony stimulating factor (bG-CSF), determined using X-ray crystallography, was used as template to develop a three-dimensional model of human IL-6 from residues 16 to 184. Firstly, the amino acid sequence of human IL-6 was aligned with that of bG-CSF. On the basis of the derived alignment, the amino acid residues in the bG-CSF three-dimensional structure were replaced by the corresponding residues of human IL-6 using molecular modelling program in a computerized interactive graphic unit. In the positions in which alignment involves either deletions or insertions (which suggests a different local structure in the interleukin 6 molecule) adjustments were made by applying the options provided by the molecular modelling program.

This three-dimensional model of interleukin 6, based on the bG-CSF structure, has enabled the identification of the two sites of interaction between human interleukin 6 and its two receptors: the low affinity receptor gp 80 (site 1) and the high affinity signal transducer receptor gp 130 (site 2). The following procedure was used to identify the two sites. From sequence comparison it is known that all the members of the family of hematopoietic receptors are related to each other by the fact that they share a domain, known as the cytokine binding domain. This similarity of sequences also indicates a high probability of structural similarity in corresponding parts of the various receptors, including the two interleukin 6 receptors, gp 80 and gp 130. The observation that the cytokines that bind to these receptors all have (or are predicted to have) a similar structure, that is a four helix bundle, strongly supports the notion that the interaction between these cytokines and their receptors, by means of the cytokine binding domain, must be very similar—albeit not identical—in biologically active complexes.

Considering that the three-dimensional structure of one of these receptor complexes (the complex made by growth hormone and the extra-cellular domain of the dimeric receptor for the growth hormone, i.e. GHbp) has been determined by means of X-ray crystallography, our bG-CSF built model of human interleukin 6 allows us to identify the potential sites of interaction between interleukin 6 and its two receptors gp 80 (site 1) and gp 130 (site 2). This has been accomplished, according to the present invention, by constructing a structural model of gp 80 and gp 130 based on the coordinates furnished by the X-ray crystallographic structure of the growth hormone receptor, and by substituting in such complex the growth hormone with our bG-CSF built model of human interleukin-6 (see FIG. 1).

As is known, interleukin 6 is a polypeptide of 184 amino acids which, as described, belongs to the class of helical cytokines. Interleukin 6 is a multi-functional cytokine produced by various cell types. It acts as a differentiation and growth factor on cells of various lineages, such as for example cells in the immune system, hepatocytes, kidney cells, hematopoietic stem cells, keratinocytes and neurones.

Production of superagonists of interleukin 6 would allow the use of therapeutic doses lower than those required with wild type interleukin 6 in the treatment of numerous serious diseases. In fact, interleukin 6 has important and promising applications in the treatment of breast cancer, leukemia, and infectious diseases or diseases connected with disorders of bone marrow progenitor cells.

In addition superagonists of IL-6 could be used in protocols for ex vivo expansion of hematopoietic progenitor cells both in bone marrow transplantation and gene therapy.

On the other hand the production of antagonists or superantagonists of human interleukin 6 would allow inhibition of interleukin 6 in numerous diseases characterized by its excessive production, such as chronic autoimmune diseases, myeloma/plasmacytoma, post-menopausal osteoporosis and cancer cachexia.

The methodology for the selection of superagonists, antagonists or superantagonists of interleukin-6, according to the present invention, comprises the following operations:

comparing the amino acid sequence of bovine granulocyte colony stimulating factor (bG-CSF) with the sequence of said hormone; and on the basis of the above comparison, formulating a three dimensional model of said hormone, which allows the identification of residues that form the site of interaction with the specific receptor (Site 1) and those that constitute the site of interaction with gp 130 (Site 2) respectively.

For selection of superagonists of interleukin 6, the methodology according to the present invention further comprises the following additional operations:

production of a series of phage libraries containing mutations of the following wild type residues of interleukin 6 (present in the form of fusion product with filamentous phage proteins): helix A: Ser 22, Glu 23, Asp 26, Arg 30, Leu 33, Ser 37, Arg 40, Glu 42; loop AB: Ser 52, Ser 53, Ala 56, Leu 57, Glu 59, Asn 60, Leu 62, Leu 64, Pro 65, Lys 66, Met 67, Ala 68, Glu 69, Lys 70, Asp 71, Phe 74, Gln 75, Ser 76; helix D: His 164, Leu 165, Arg 168, Ser 169, Lys 171, Glu 172, Phe 173, Gln 175, Ser 176, Ser 177, Leu 178, Arg 179, Ala 180, Leu 181, Arg 182, Gln 183, Met 184.

selection, from the mixed population of phages belonging to each individual phage library and expressing interleukin 6 mutants, of that or those with an affinity for the specific receptor greater than that of wild type interleukin; and identification of the best receptor binding amino acid sequence or sequences by sequencing of the DNA extracted from the selected phage particles.

In this case, a series of phage libraries can be produced containing mutations of said wild type residues of interleukin 6 present as a fusion product with the M13 pIII protein.

The methodology for selecting antagonists of interleukin 6 according to the present invention comprises—along with the operations indicated above for molecular modelling of the human IL-6 protein and its receptor chains—the following operations:

mutagenesis of the residues identified to form part of the site of interaction with gp 130 (Arg 30, Tyr 31, Gly 35, Ser 37, Ala 38, Ser 118, Lys 120, Val 121, Gln 124, Phe 125, Gln 127, Lys 128 and Lys 129), using conventional molecular biology techniques;

evaluation of biological activity and affinity for the specific interleukin 6 receptor of the mutants produced as above, in order to identify variants of interleukin 6 whose affinity for the specific receptor is normal and that show reduction or loss of the biological activity; and evaluation of the above variants of interleukin 6 as antagonists for the biological activity of wild type interleukin 6 on human cell lines.

In case of obtaining of superantagonists of interleukin 6 by combination of the variants of amino acid sequences responsible for antagonist activity, identified as above, with amino acid mutations responsible for an increased affinity of the specific receptor for interleukin 6.

In the methodology for obtaining antagonists or superantagonists of interleukin 6, the mutagenesis of the residues identified as above can be performed using a molecular biology technique chosen from the group comprising Polymerase Chain Reaction, Primer Extension, Oligonucleotide Directed Mutagenesis, and combinations thereof.

The present invention is not limited to the methodology for selection of superagonists, antagonists or superantagonists of interleukin 6. On the contrary, it extends to molecules obtainable by said methodology of selection, i.e. to: superagonists of h IL-6, with the exception of the molecule called IL-6 IRA and carrying the following three substitutions Gln175Ile/Ser176Arg/Gln183Ala; antagonists of h IL-6, with the exception of three molecules with the following substitutions: Tyr31Asp/Gly35Phe/Ser118Arg/Val121Asp (DFRD) Tyr31Asp/Gly35Phe/Ser118Phe/Val121Asp (DFFD) Tyr31Asp/Gly35Phe/Ser118Leu/Val121Asp (DFLD); and superantagonists of h IL-6, with the exception of the molecule called Sant1 and carrying the following seven substitutions: Tyr31Asp/Gly35Phe/Ser118Arg/Val121Asp/Gln175Ile/Ser176Arg/Gln183Ala.

Up to this point a general description of the subject of the present invention has been given. With the aid of the following examples a detailed description of specific embodiments of the invention will now be given, with the purpose of giving a better understanding of the objects, characteristics, advantages and methods of application thereof.

DEPOSITS

Figure 1:
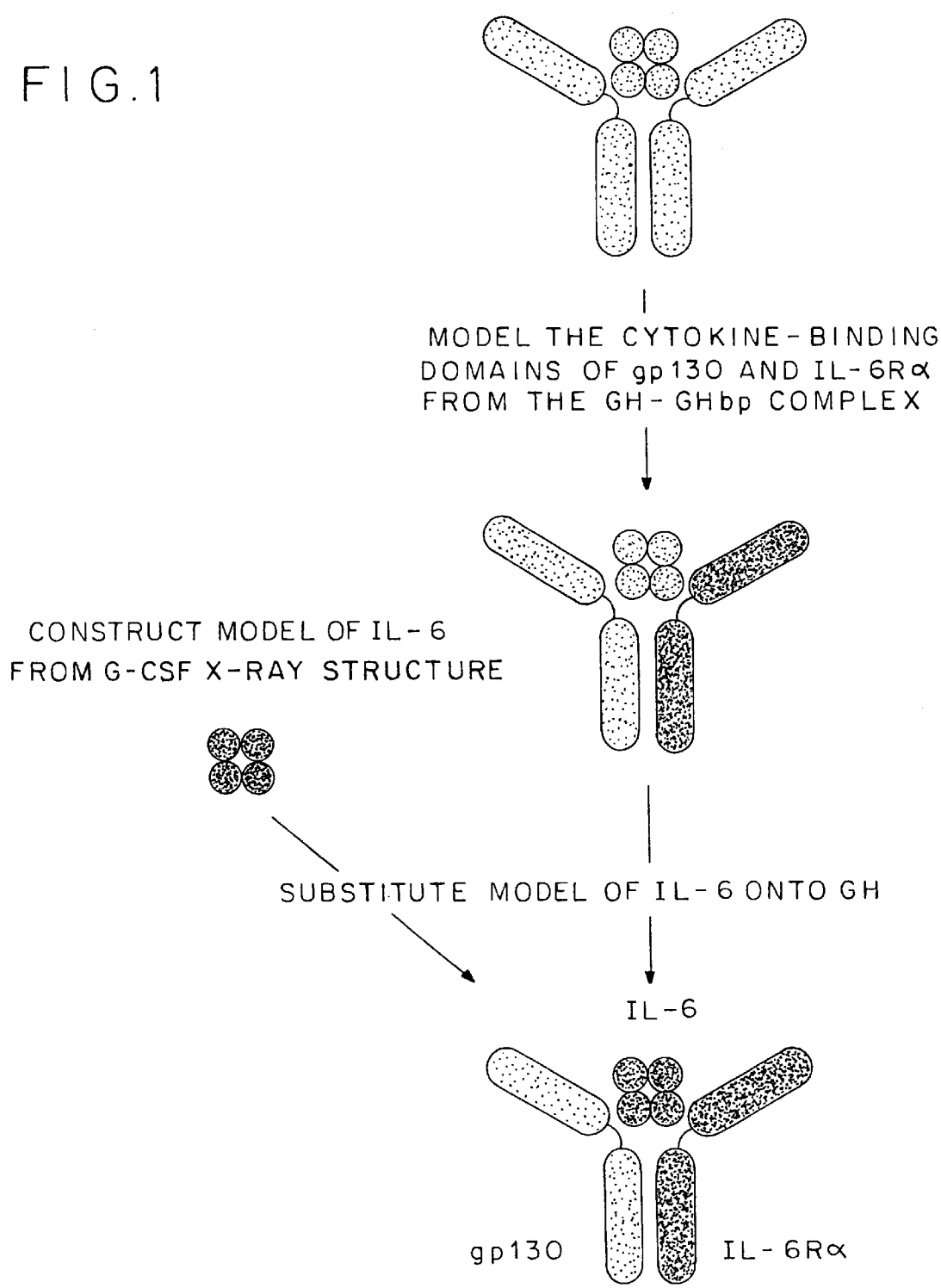
FIG. 1 shows a scheme illustrating the methodology applied to identify site 1 and site 2 in the case of human interleukin 6.

E.coli K12 bacteria—transformed using the plasmid pHenΔhIL-6 containing, from the recognition site of the restriction enzyme SalI to that for the restriction enzyme NotI, a nucleotidic sequence coding for the amino acid sequence of wild type human interleukin 6 —have been deposited on Oct. 6, 1993 with The National Collection of Industrial and Marine Bacteria Ltd. (NCIMB), Aberdeen, Scotland, UK, with access number NCIMB 40563.

EXAMPLE 1

Application of the methodology according to the present invention for the selection of superagonists interleukin 6 by means of mutagenesis of amino acid residues in the AB loop The strategy consists in construction of a hybrid gene containing all the region coding for hIL-6 (SEQ ID NO:1) followed by the last 157 amino acids of protein pIII of the phage M13 and preceded by the sequence Pel B, which vectors the synthesized protein to the periplasmic space.

This construct allows the obtaining of phagemid particles displaying on their surface correctly folded and biologically active human interleukin 6.

A phage library was constructed containing mutations of residues Asp 71, Phe 74, Gln 75 and Ser 76 of interleukin 6, starting from the variant IL-6 IRA (substitutions Gln175Ile/Ser176Arg/Gln183Ala) described in WO95/00852 and having an affinity for the receptor approximately five times greater than that of wild type human interleukin 6, present in the form of fusion product with protein pIII of filamentous phage M13. The library was constructed using the Primer Extension technique. The mutagenic oligonucleotide is IL-6 DFQS, a 95 nucleotides oligo, whose sequence is SEQ ID NO: 2. Primer IL-6 DFQS introduces degenerations into codons coding for the amino acids 71 (wild type Asp), 74 (wild type Phe), 75 (wild type Gln) and 76 (wild type Ser). The oligonucleotide IL-6 AB primer, whose sequence is SEQ ID NO: 3, was used as primer for the Primer Extension reaction. The two oligonucleotides were annealed in vitro, and the annealed oligonucleotides were used as substrate for a Primer Extension reaction. The double-stranded DNA fragment thus obtained was then digested and ligated into the plasmid pHenΔhIL-6 in order to replace the wild type sequence with the mutated ones. The ligation product was inserted in bacteria, yielding roughly three million independent transformants. The transformed bacteria were infected with the M13K07 helper bacteriophage to generate the phage library (a library of phasmids).

The library underwent selection by incubation with magnetic beads coated with monoclonal antibody directed against shrIL-6R and in the presence of shrIL-6R and shrgp130. The phasmid population eluted at pH 3.6 was then amplified in bacteria. After four cycles of selection-amplification, randomly selected phasmids were sequenced over the mutagenized region, the corresponding mutant interleukin 6 proteins were produced in the periplasmic space of the appropriate bacterial strain and tested for interleukin 6 specific receptor binding. Table 1 shows that, using the methodology according to the present invention, it is possible to select variants of interleukin 6 having an additional increase in the affinity for the specific receptor, molecules with mutations both in helix D and in region A–B.

TABLE 1

Receptor binding properties in variants of interleukin 6-IRA containing additional mutations in the residues 71, 74, 75 and 76 of the region A-B.

| Position | 71 | 74 | 75 | 76 | Receptor binding (%) |
|---|---|---|---|---|---|
| wild type | Asp | Phe | Gln | Ser | 100% |
| IL-6IRA | Asp | Phe | Gln | Ser | 450% |
| phasmid D3-3 | Asp | Tyr | Phe | Ile | 2350% |
| phasmid D4-1 | Asp | Tyr | Tyr | Val | 2750% |
| phasmid D3-7 | Asp | Phe | Tyr | Ile | 2770% |
| phasmid D4-19 | Asp | Tyr | Tyr | Ser | 1800% |
| phasmid D4-20 | Asp | Phe | Tyr | Lys | 4200% |
| phasmid D3-16 | Asp | Phe | Tyr | Leu | 1450% |
| phasmid D4-17 | Asp | Phe | Phe | Ile | 2430% |

EXAMPLE 2

Application of the methodology according to the present invention for obtaining superantagonists of interleukin 6

The four mutations Tyr31Asp/Gly35Phe/Ser118Arg/Val121Asp (DFRD) confer antagonistic properties as described in WO95/00852. These four mutations were combined with mutations capable of increasing the specific receptor binding capacity (described in example 1), using the Polymerase Chain Reaction (PCR) molecular biology technique. More specifically:

the super-binder mutations on helix D and region AB of the phasmid D 3–7 (described in example 1), to create the mutant protein Sant 3;

the super-binder mutations on helix D and region AB of the phasmid D 3—3 (described in example 1), to create the mutant protein Sant 4;

the super-binder mutations on helix D and region AB of the phasmid D 4–20 (described in example 1), to create the mutant protein Sant 5.

Figure 2:
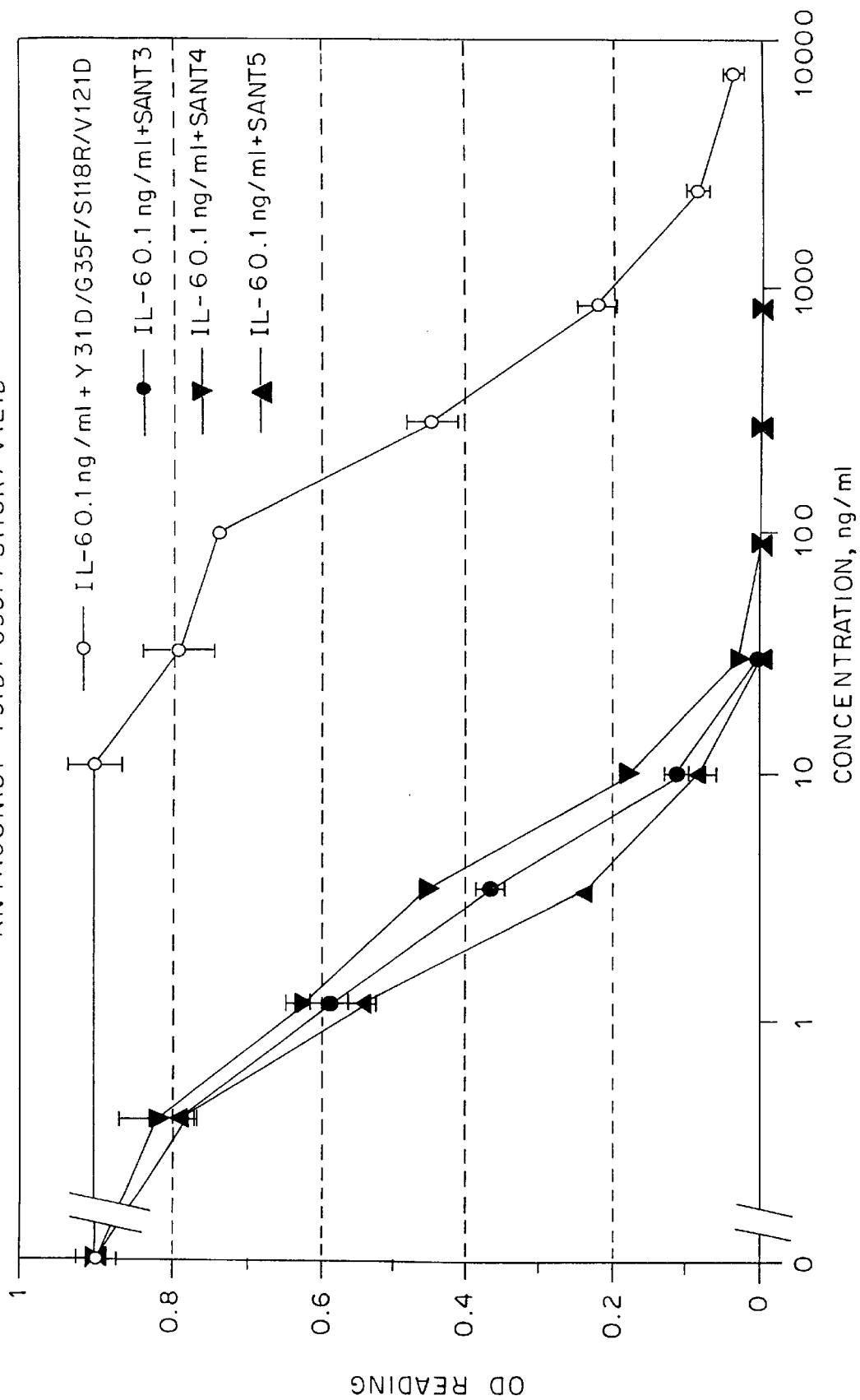
FIG. 2 shows the increase in potency of three superantagonists according to the invention, i.e. Sant 3, Sant 4 and Sant 5, over antagonist Tyr31Asp/Gly35Phe/Ser118Arg/Val121Asp (the one letter codes have been used in the figure), with the increase of concentration.

The mutant proteins, containing nine (Sant 3 and Sant 5) or ten (Sant 4) amino acid substitutions, were tested both for their specific interleukin-6 receptor binding, and for their ability to antagonize the biological activity of interleukin-6 on human hepatoma and myeloma cells. Table 2 and FIG. 2 show the specific receptor binding properties of DFRD and of Sant 3, Sant 4 and Sant 5 along with the concentrations (expressed in nanograms of mutant per milliliter of culture medium) of mutant necessary to inhibit 50% of interleukin 6 biological activity (hepatoma cells were stimulated with 4 nanograms of wild type interleukin 6 per milliliter of culture medium, while myeloma cells were stimulated with 0.1 nanograms of interleukin 6 per milliliter of culture medium, due to the higher sensitivity of the latter cells to wild type interleukin 6).

TABLE 2

Inhibition of wild type interleukin 6 biological activity on both human hepatoma and myeloma cells as a function of the mutant antagonists' specific interleukin-6 receptor binding capacity

| | Receptor | 50% inhibition of interleukin 6 activity on: | |
|---|---|---|---|
| Antagonist | binding (% of wild type) | hepatoma cells Hep3B | myeloma cells XG-1 |
| DFRD | 97% | 164 ng/ml | 190.0 ng/ml |
| Sant 3 | 2800% | 2.4 ng/ml | 1.85 ng/ml |
| Sant 4 | 2000% | 2.7 ng/ml | 3.90 ng/ml |
| Sant 5 | 4500% | 2.3 ng/ml | 2.45 ng/ml |

As can be seen from the table, the introduction of the amino acid substitutions described in example 1 has at once increased the specific receptor binding capacity of the parental mutant DFRD and decreased the amount of antagonist needed to inhibit 50% of wild type interleukin 6 biological activity on both cell lines tested, therefore generating very effective and strong interleukin 6 superantagonists.

We claim:

1. An interleukin-6 receptor antagonist having an amino acid sequence of wild-type human interleukin-6 comprising a set of amino acid substitutions selected from the group consisting of:

(1) Tyr31Asp, Gly35Phe, Gln75Tyr, Ser76Ile, Ser118Arg, Val121Asp, Gln 175Ile, Ser176Arg, Gln183Ala;

(2) Tyr31Asp, Gly35Phe, Phe74Tyr, Gln75Phe, Ser76Ile, Ser 118Arg, Val121Asp, Gln175Ile, Ser176Arg, Gln183Ala; and (3) Tyr31Asp, Gly35Phe, Gln75Tyr, Ser76Lys, Ser118Arg, Val121Asp, Gln175Ile, Ser176Arg, Gln183Ala.

2. The interleukin-6 receptor antagonist according to claim 1, which comprises a set of amino acid substitutions Tyr31Asp, Gly35Phe, Gln75Tyr, Ser76Ile, Ser118Arg, Val121Asp, Gln175Ile, Ser176Arg, Gln183Ala.

3. A composition comprising the interleukin-6 receptor antagonist of claim 2 in a pharmaceutically effective carrier, vehicle or auxiliary agent.

4. The interleukin-6 receptor antagonist according to claim 1, which comprises a set of amino acid substitutions Tyr31Asp, Gly35Phe, Phe74Tyr, Gln75Phe, Ser76Ile, Ser118Arg, Val121Asp, Gln175Ile, Ser176Arg, Gln183Ala.

5. A composition comprising the interleukin-6 receptor antagonist of claim 4 in a pharmaceutically effective carrier, vehicle or auxiliary agent.

6. The interleukin-6 receptor antagonist according to claim 1, which comprises a set of amino acid substitutions Tyr31Asp, Gly35Phe, Gln75Tyr, Ser76Lys, Ser118Arg, Val121Asp, Gln175Ile, Ser176Arg, Gln183Ala.

7. A composition comprising the interleukin-6 receptor antagonist of claim 6 in a pharmaceutically effective carrier, vehicle or auxiliary agent.

* * * * *

UNITED STATES PATENT AND TRADEMARK OFFICE
CERTIFICATE OF CORRECTION

PATENT NO. : 5,849,283
DATED : Dec. 15, 1998
INVENTOR(S) : Ciliberto et al.

It is certified that error appears in the above-identified patent and that said Letters Patent is hereby corrected as shown below:

Cover page, item [30], delete "M94A00805" and insert therefor --RM 94A000805--.

Signed and Sealed this

Twenty-second Day of June, 1999

Attest:

Q. TODD DICKINSON

Attesting Officer

Acting Commissioner of Patents and Trademarks